US00PP16960P2

(12) United States Plant Patent
Pieters

(10) Patent No.: US PP16,960 P2
(45) Date of Patent: Aug. 8, 2006

(54) ***CHRYSANTHEMUM* PLANT NAMED 'PPP PAD L05'**

(50) Latin Name: *Chrysanthemum morifolium*
Varietal Denomination: PPP PAD L05

(75) Inventor: Dirk Pieters, Ooostnieuwkerke (BE)

(73) Assignee: Pieters Plant Production BVBA, Oosnieuwkerke (BE)

( * ) Notice: Subject to any disclaimer, the term of this patent is extended or adjusted under 35 U.S.C. 154(b) by 0 days.

(21) Appl. No.: 11/115,705

(22) Filed: Apr. 27, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
*Assistant Examiner*—Annette H Para
(74) *Attorney, Agent, or Firm*—Albert O. Cota

(57) ABSTRACT

A new and distinct *Chrysanthemum* plant cultivar is disclosed, characterized by large decorative type inflorescences, consistent flowering response to short days, blooming consistently after 49 days of short day length, bright yellow ray florets, free branching habit, and a consistent natural season flowering habit during the first week of September.

1 Drawing Sheet

Figure 1:
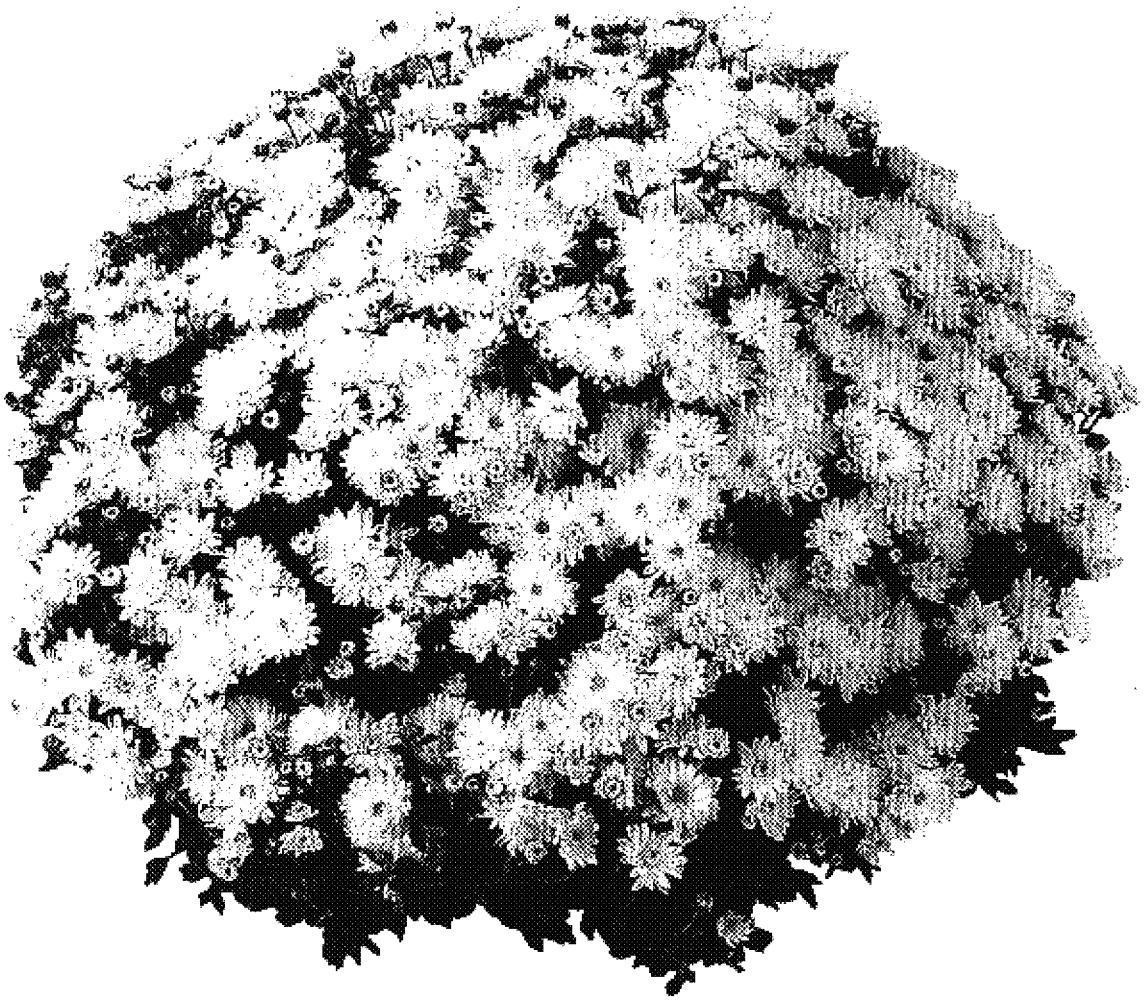

Latin name of the genus and species: *Chrysanthemum morifolium.*
Variety denomination: 'PPP PAD L05'.

BACKGROUND OF THE INVENTION

The new cultivar 'PPP PAD L05' is a product of an induced mutation of the parent *Chrysanthemum* plant variety 'Gedi Two Pad' (U.S. Plant Pat. No. 14,501) using gamma ray treatment at a dose of 20 Gy. The new cultivar was discovered and selected by Dirk Pieters in September 2003 in Oostnieuwkerke, Belgium.

Asexual reproduction of the new cultivar 'PPP PAD L05' by terminal cuttings and tissue culture was performed in Oostnieuwkerke, Belgium, and has shown that the unique features of this new cultivar are stable and reproduced true to type on successive generations.

SUMMARY OF THE INVENTION

The cultivar 'PPP PAD L05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP PAD L05.' These characteristics in combination distinguish 'PPP PAD L05' as a new and distinct *Chrysanthemum* cultivar:

1. Large decorative inflorescence;
2. Consistent flowering response to short days, blooming consistently after 49 days of short day length;
3. Free branching habit; and
4. Consistent natural season flowering habit during the first week of September.

Plants of the new cultivar 'PPP PAD L05' are similar to plants of the parent variety, 'Gedi Two Pad,' in most horticultural characteristics, however plants of the new cultivar 'PPP PAD L05' has more ray florets than the ray florets of the parent variety 'Gedi Two Pad.' Additionally, the new variety is shorter than the parent and also has different color ray florets than the parent.

In comparison to the commercially available variety 'Gedi One Ylcel' (U.S. Plant Pat. No. 13,903), 'PPP PAD L05' has different yellow ray florets. Additionally, the new variety 'PPP PAD L05' naturally blooms approximately two weeks earlier than the comparable variety. Further, the new variety 'PPP PAD L05' has more inflorescence per flowering branch and is taller than the comparable variety 'Gedi One Ylcel.'

BRIEF DESCRIPTION OF THE PHOTOGRAPH

The accompanying photograph in FIG. 1 illustrates in full color a typical plant of 'PPP PAD L05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP PAD L05' plants grown in Oxnard, Ventura County, Calif., during the month of September 2004. The growing temperature ranged from 12° C. to 15° C. at night to 12° to 20° during the day. Measurements and numerical values represent averages of typical flowering types.

Botanical classification: *Chrysanthemum morifolium* cultivar 'PPP PAD L05.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 26 cm.
Plant spread: Approximately 32 cm.
Growth rate: Moderate.
Branching characteristics: Free Branching.
Length of lateral branches: Approximately 18 cm.
Number of leaves per lateral branch: Approximately 13.
Age of plant described: Approximately 146 days.

FOLIAGE

Leaf:
*Arrangement.*—Alternate single.
*Average length.*—Approximately 5.2 cm.
*Average width.*—Approximately 3.7 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1.3 cm.
*Color.*—Young foliage upper side: Near Green 137A. Young foliage under side: Near Green 138A. Mature foliage upper side: Near Green 137A. Mature foliage under side: Near Green 137A.
*Venation.*—Type: Palmately net. Venation color upper side: Near Green 138C. Venation color under side: Near Green 138C.
Petiole:
*Average length.*—Approximately 2.2 cm.
*Color.*—Near Green 138A.
*Diameter.*—Approximately 0.87 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately first week in September.
*Number of inflorescences per lateral branch.*—Approximately 22.
*Inflorescence diameter.*—Approximately 4.8 cm.
*Inflorescence depth.*—1.7 cm.
*Inflorescence longevity on plant.*—Approximately 25 days.
*Persistence.*—Persistent.
Ray florets:
*Appearance.*—Matte.
*Texture.*—Smooth.
*Average number of ray florets per inflorescence.*—150.
*Shape.*—Oblanceolate.
*Aspect.*—Flat.
*Margin.*—Entire.
*Apex.*—Obtuse.
*Length.*—Approximately 2.2 cm.
*Width.*—Approximately 1 cm.
*Color.*—Upper surface at first opening: Near Yellow 4A. Upper surface at maturity: Near Yellow 2B. Upper surface at fading: Near Yellow 3C. Under surface at first opening: Near Yellow 4A. Under surface at maturity: Near Yellow 2A. Under surface at fading: Near Yellow 3C.
Disc florets:
*Appearance.*—Shiny.
*Texture.*—Smooth.
*Average number of florets per disc.*—Approximately 20.
*Shape.*—Cylindric.
*Apex.*—Obtuse.
*Average length.*—Approximately 0.7 cm.
*Average width.*—Approximately 0.2 cm.
*Color.*—At first opening: Near Yellow 7A. At maturity: Near Yellow 7A. At fading: Near Yellow 13B.
Peduncle:
*Length.*—At terminal end (shortest): Approximately 3.3 cm. At lateral end (longest): Approximately 7.2 cm.
*Angle to stem.*—Acute.
*Strength.*—Moderate.
*Color.*—Near Green 137C.
*Habit.*—Upright.
*Diameter.*—0.3 cm.
*Surface texture.*—Lightly pubescent.
Inflorescence bud:
*Length.*—Approximately 1 cm.
*Diameter.*—Approximately 1 cm.
*Form.*—Globular.
*Color.*—Near Yellow 4A.
Involucral bracts (phyllaries):
*Appearance.*—Matte.
*Texture.*—Lightly pubescent.
*Number.*—Approximately 20.
*Shape.*—Ovate.
*Margin.*—Entire.
*Apex.*—Acute.
*Length.*—1 cm.
*Width.*—0.8 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow Orange 16D.
*Style color.*—Near Yellow 2B.
*Style length.*—0.6 cm.
*Stamens.*—Absent.
Disc florets:
*Number of pistils per floret.*—1.
*Stigma shape.*—Cylindric.
*Stigma color.*—Near Yellow 8B.
*Style length.*—0.5 cm.
*Style color.*—Near Yellow-Green 154A.
*Number of stamens per floret.*—Approximately 5.
*Anther shape.*—Tubular.
*Anther color.*—Near Yellow-Orange 16A.
*Pollen color.*—Near Yellow-Orange 17B.

OTHER CHARACTERISTICS

Disease resistance: Neither resistance nor susceptibility to diseases or pests has been observed in this variety.
Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP PAD L05' as herein illustrated and described.

* * * * *